(12) United States Patent
Gumbrecht et al.

(10) Patent No.: US 8,753,874 B2
(45) Date of Patent: *Jun. 17, 2014

(54) BIOCHIP

(75) Inventors: Walter Gumbrecht, Herzogenaurach (DE); Manfred Stanzel, Erlangen (DE)

(73) Assignee: Siemens Aktiengesellschaft, Munich (DE)

( * ) Notice: Subject to any disclaimer, the term of this patent is extended or adjusted under 35 U.S.C. 154(b) by 929 days.

This patent is subject to a terminal disclaimer.

(21) Appl. No.: 10/540,208

(22) PCT Filed: Dec. 15, 2003

(86) PCT No.: PCT/DE03/04137
§ 371 (c)(1),
(2), (4) Date: Nov. 16, 2005

(87) PCT Pub. No.: WO2004/057335
PCT Pub. Date: Jul. 8, 2004

(65) Prior Publication Data
US 2006/0137984 A1    Jun. 29, 2006

(30) Foreign Application Priority Data
Dec. 19, 2002 (DE) .................................. 102 59 821

(51) Int. Cl.
| | |
|---|---|
| *C12M 1/34* | (2006.01) |
| *C12M 3/00* | (2006.01) |
| *C12M 1/00* | (2006.01) |
| *C02F 1/40* | (2006.01) |
| *B03C 5/02* | (2006.01) |
| *G01N 15/06* | (2006.01) |
| *G01N 27/00* | (2006.01) |
| *G01N 33/00* | (2006.01) |
| *C07H 21/02* | (2006.01) |

(52) U.S. Cl.
USPC ...... 435/287.2; 435/6.1; 435/283.1; 204/600; 204/643; 422/68.1; 422/82.01; 536/23.1

(58) Field of Classification Search
CPC .................................................. G01N 33/5438
USPC .................... 435/283.1, 287.2; 204/600, 643; 422/68.1, 82.01; 536/23.1
See application file for complete search history.

(56) References Cited

U.S. PATENT DOCUMENTS 6,372,813 B1 * 4/2002 Johnson et al. ................ 522/114
6,485,703 B1 * 11/2002 Cote et al. ...................... 424/9.1

(Continued)

FOREIGN PATENT DOCUMENTS

| | | |
|---|---|---|
| DE | 44 26 507 C2 | 2/1996 |
| DE | 196 10 115 A1 | 9/1997 |

(Continued)

OTHER PUBLICATIONS

Datasheet dimethylacrylate, Retrieved from the internet URL:http//chemicalregister.com/3_3-Dimethylacrylic_acid/suppliers/pid28139.htm, printed Nov. 23, 2010.*

(Continued)

*Primary Examiner* — Narayan Bhat
(74) *Attorney, Agent, or Firm* — Harness, Dickey & Pierce, P.L.C.

(57) ABSTRACT

A biochip includes a flat carrier and an array of spots containing catcher molecules which are arranged on the carrier. Each spot is associated with a microelectrode arrangement for impedance spectroscopic detection of binding events occurring between the catcher molecules and the target molecules applied via an analyte solution. In order to increase the sensitivity or the binding-specific measuring effects of the bio-chip, the electrode arrangement is at least partially embedded in a hydrophilic reaction layer containing catcher molecules and which is permeable to target molecules.

16 Claims, 3 Drawing Sheets

(56) References Cited

U.S. PATENT DOCUMENTS

| | | | |
|---|---|---|---|
| 6,518,022 B1* | 2/2003 | Sosnowski et al. | 435/6.11 |
| 6,845,327 B2 | 1/2005 | Lauks | |
| 7,208,077 B1* | 4/2007 | Albers et al. | 205/782 |
| 2002/0028441 A1 | 3/2002 | Hintsche et al. | |
| 2002/0102415 A1* | 8/2002 | Valint et al. | 428/447 |
| 2002/0179444 A1 | 12/2002 | Lauks | |
| 2003/0000833 A1* | 1/2003 | Mansouri et al. | 204/402 |
| 2003/0148530 A1 | 8/2003 | Lauks | |
| 2004/0121339 A1* | 6/2004 | Zhou et al. | 435/6 |

FOREIGN PATENT DOCUMENTS

| | | | |
|---|---|---|---|
| DE | WO 00/62048 | * | 10/2000 |
| DE | 200 22 642 U1 | | 4/2002 |
| JP | 5-093709 | | 4/1993 |
| JP | 2002-088652 | | 3/2002 |
| WO | WO 97/34140 | | 9/1997 |
| WO | WO 98/19153 A1 | | 5/1998 |
| WO | WO 00/62047 A1 | | 10/2000 |
| WO | WO 00/65097 A1 | | 11/2000 |
| WO | WO 02/41992 A2 | | 5/2002 |

OTHER PUBLICATIONS

Proudnikov D. et al. "Immobilization of DNA in polyacrylamide gel for the manufacture of DNA and DNA-oligonucleotide microchips", Analytical Biochemistry, Academic Press, Bd. 259, 1998, S. 34-41.

Marquette Christophe A. et al: "Regnerable immunobiosensor for the chemiluminescent flow injection analysis of the herbicide 2, 4-D", Jul. 2, 2000, vol. 51, Nr. 2, S. 395-401.

English translation of Japanese Notice of Reasons for rejection for Counterpart Japanese Patent Application No. 2004-561041.

* cited by examiner

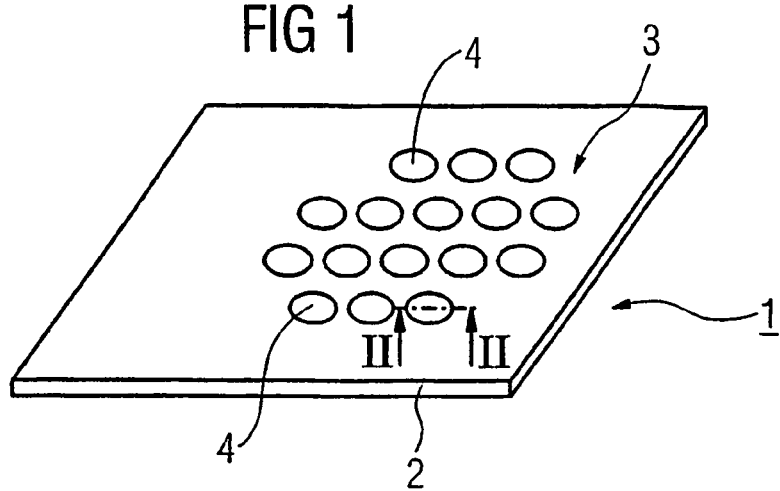
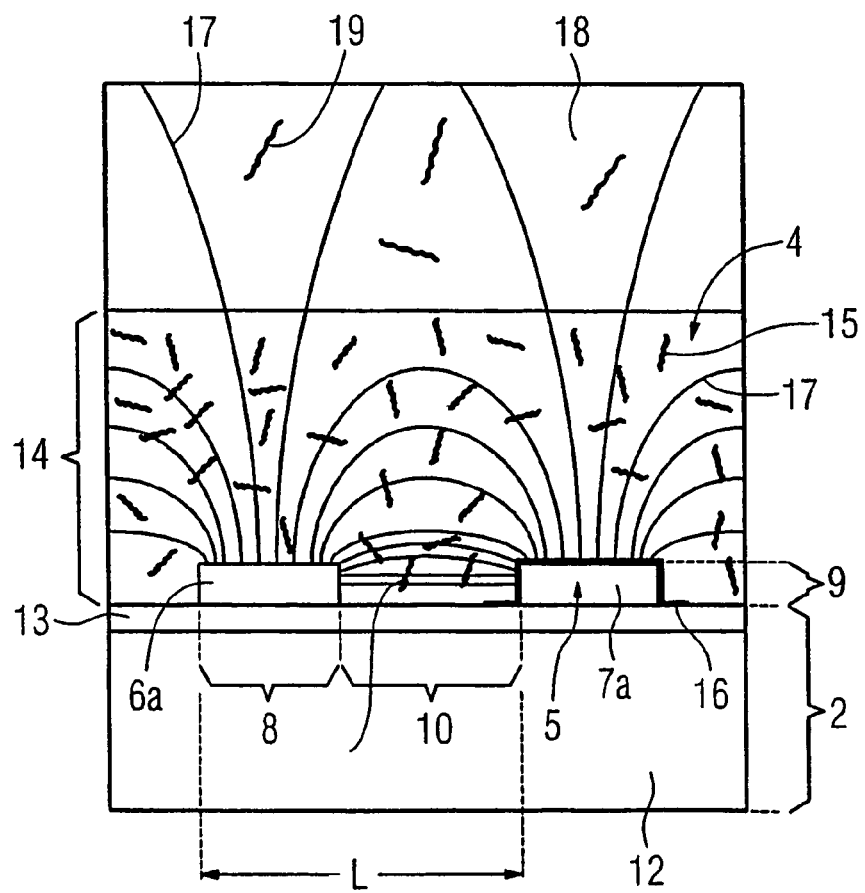

BIOCHIP

This application is a PCT National Stage Application of PCT/DE2003/004137 filed Dec. 15, 2003, which claims priority under on German Patent Application No. DE 102 598 21.5 filed in Germany on Dec. 19, 2002, the entire contents of which is hereby incorporated herein by reference.

FIELD

The invention generally relates to a biochip, in particular a DNA chip.

BACKGROUND

Biochips or DNA chips include a flat carrier, on one side of which at least one spot array, that is to say a gridlike arrangement of analysis positions, is present. The spots contain probe or catcher molecules, for example oligonucleotides, immobilized on the carrier surface. Target molecules, for example DNA fragments, contained in an analyte solution applied to a spot couple to the catcher molecules. The conversion of such coupling or binding events into detectable signals is effected by means of optical, piezoelectric, electrochemical, calorimetric or impedance-spectroscopic methods.

In the case of an impedance-spectroscopically readable DNA chip disclosed in DE 196 10 115 C2, an interdigital electrode arrangement is present on a sensor area, catcher molecules being immobilized on the electrodes and the areas arranged between the electrodes. The coupling of target molecules to the catcher molecules leads, e.g. on account of charge changes, to a change in the alternating electric field generated by the electrodes or generally to a change in an electrical property in the vicinity of the electrodes, e.g. the impedance. A measurement of an impedance change can be carried out by way of a, for example, two-pole interdigital electrode arrangement in which the electrodes are formed from a plurality of partial electrodes.

What is problematic with the last manner of detecting binding events is that the dimensions of the electrode structures differ by orders of magnitude from molecular dimensions. With a technical outlay that is still tenable, it is possible to produce electrodes whose width and spacing, taken together, have a value L (=width+spacing) of approximately 2 to 20 µm and a height of approximately 0.1 to 0.5 µm.

The impedance-spectroscopically detectable range of the electric field of such an electrode arrangement extends approximately 1 to 5 L (=2 to 100 µm) beyond the carrier surface or the planar plane spanned by the electrode arrangement. By contrast, a catcher molecule having 100 base pairs, for example, has a length of only approximately 30 nm. The influence of binding events in a monomolecular layer of catcher molecules that is immobilized on the sensor surface or the electrodes on the electric field is correspondingly low, particularly when only few binding processes take place. The publication "Nanoscaled interdigitated electrode arrays for biochemical sensors", P. van Gerwen et al, Sensors and Actuators B 49, 1998, 72-80, proposes, for solving the problem discussed, approximating the dimensions of electrode structures to the dimensions of DNA target molecules, electrode structures with partial electrodes being sought whose widths and mutual spacings lie approximately in the range of 250 to 500 nm. However, such dimensions are associated with an increased production outlay.

Furthermore, WO 98/19153 A1 discloses a sensor for biochemical applications which contains electrodes embedded in a conductive polymer. In this case, the conductive polymer is in contact with the analyte in which a biochemical process takes place as a result of alternating-current influencing. In this case, process changes by way of the conductive polymer are forwarded as impedance changes to the electrode system and detected.

The sensitivity of a sensor chip constructed in this way is problematic. Moreover, embedding or coating the electrodes in a conductive polymer is complicated, so that the biosensor described is not practically suitable.

SUMMARY

It is an object of an embodiment of the invention to propose an impedance-spectroscopically readable DNA chip with improved sensitivity which can be produced cost-effectively.

In the case of an embodiment of the invention, the electrode arrangement is at least partially embedded in a hydrophilic reaction layer which is permeable to target molecules and in which immobilized catcher molecules are distributed three-dimensionally. In this case, the reaction layer is dimensioned such that it is pervaded by the predominant part of the electric field generated by the electrode arrangement or by the impedance-spectroscopic detection range thereof.

An advantage of a biochip according to an embodiment of the invention resides in the fact that a significantly larger number of catcher molecules can be arranged within the reaction layer than in a monomolecular layer on the carrier surface and on the surfaces of the electrodes. Added to this, however, is the fact that the dimensioning of the reaction layer is adapted to the space pervaded by the electric field or by the field lines thereof, so that a large number or a high concentration of catcher molecules is present with an approximately homogeneous distribution within the detection range mentioned. The consequence is a much greater influencing of the electric field or of the impedance-spectroscopic detection range of the electrode arrangement. A DNA chip configured in this way has a correspondingly greater measurement sensitivity, or sensitivity.

The thickness of the reaction layer should advantageously be at most 100 µm. In practice, however, the thickness of the reaction layer must not be chosen to be too large because this would result in excessively long diffusion paths and, associated therewith, excessively long reaction times for the transport of the target molecules to the catcher molecules.

Given electrode widths in the region of approximately 1 µm and the same spacings, the thickness of the reaction layer is between 2 and 10 µm, for example approximately 3 µm in the case of a two-pole microelectrode system and approximately 7 µm in the case of a four-pole microelectrode system.

In a preferred refinement of an embodiment, the reaction layer has a thickness laying approximately in the range of 1-5 L, where L is the sum of electrode width and electrode spacing. This ensures that, on the one hand, a region of the electric field with a relatively high field line density is utilized for detecting binding events and, on the other hand, the thickness of the reaction layer is not so large that it impedes the indiffusion of target molecules and reactants.

With a reaction layer that is thermally stable up to approximately 95° C., a DNA chip of the type under discussion can be employed for PCR reactions. In this case, thermally stable is intended to mean that the reaction layer, even at the temperature mentioned, is configured in such a way that it does not resolve, that it fixedly retains catcher molecules, that reactions between target and catcher molecules can take place unimpeded in it, and that it also essentially maintains its other properties.

In a further preferred refinement of an embodiment, the reaction layer contains polymers with coupling groups to which catcher molecules are covalently bound. As such, binding pairs including target and catcher molecules are retained in the reaction layer in the event of rinsing operations during the analysis procedure. A particularly suitable reaction layer comprises a hydrogel. Hydrogels form an aqueous milieu in a mechanically stable form which permits a substance exchange with a predominantly aqueous analyte. Acrylamide-based radical-crosslinkable hydrogels with maleic anhydride and/or glycidyl (meth)acrylate as coupling groups have proved to be particularly suitable.

In a further preferred embodiment, the flat carrier of the DNA chip comprises a silicon layer and an insulating layer connected thereto, the latter carrying the electrode arrangement and the reaction layer on its side remote from the silicon layer. In the case of such an arrangement, it is possible to realize the electrical interconnection of the electrode structure with analog and digital circuits known from Si semiconductor technology.

BRIEF DESCRIPTION OF THE DRAWINGS

Further details and advantages of the invention emerge from the description of figures of example embodiments with reference to the drawings. In the figures:

FIG. 1 shows a simplified perspective illustration of a biochip including a flat carrier and a spot array, FIG. 2 shows a cross section through a spot in accordance with line II-II in FIG. 1, in an enlarged detail illustration.

DETAILED DESCRIPTION OF THE EXAMPLE EMBODIMENTS

Figure 3:
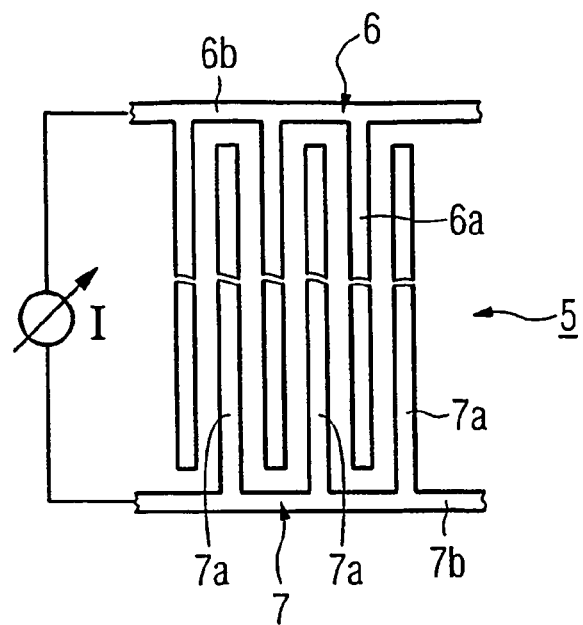
FIG. 3 shows a detail from an electrode arrangement assigned to a spot.

As shown in FIG. 1, a biochip 1 includes a flat carrier 2, on one side of which a spot array 3 is applied. A spot 4 contains immobilized catcher molecules, for example oligonucleotides. If an analyte solution with unknown target molecules is applied to a spot, then the target molecule is coupled to the catcher molecule in the event of corresponding matching in the base sequence. The property change brought about by such a binding event, e.g. changes in the resistivity or the dielectric constant, is detected impedance-spectroscopically by way of an electrode arrangement 5.

A 2-pole electrode arrangement is present in the case of the example embodiment of FIG. 2. This arrangement is applied to the flat carrier 2 for example with the aid of a photolithographic method. The electrode arrangement 5 includes two electrodes 6, 7 designed in the form of an interdigital structure. That is to say that each electrode includes a plurality of strip-type partial electrodes 6a, 7a which run parallel to one another and in each case extend into the inter-space between two partial electrodes of the respective other electrodes. The partial electrodes 6a, 7a are connected to one another by a likewise strip-type connecting conductor 6b, 7b extending transversely with respect to the partial electrodes 6a, 7a.

An AC voltage e.g. in the megahertz range is applied to the electrodes 6, 7. The width 8 of the partial electrodes 6a, 7a is approximately 1 µm, their height 9 is approximately 100 to 500 nm. A spacing 10 of likewise approximately 1 µm is present between the partial electrodes 6a, 7a.

The flat carrier 2 includes a silicon layer 12 and an insulating layer 13 e.g. made of silicon dioxide or silicon nitride that is arranged between said silicon layer and the electrodes 6, 7. The electrical interconnections and components required for the impedance-spectroscopic measurement of binding events are realized in a conventional manner by means of a corresponding patterning of the silicon layer (not illustrated). A reaction layer 14 made of a hydrogel is applied on the insulating layer 13, which hydrogel is described in more detail further below.

Catcher molecules 15 are embedded and homogeneously distributed in the reaction layer 14 or the hydrogel, said catcher molecules being illustrated symbolically and in overdimensioned fashion in FIG. 2. A catcher molecule with 300 bases has approximately a length of 100 nm. Accordingly, a monomolecular layer of catcher molecules in the case of conventional biochips has at most approximately a thickness corresponding to the line 16 in FIG. 2.

It is readily apparent that such a layer can take up relatively few catcher molecules 15 and, correspondingly, can influence the electric field only to a small extent in the case of binding events. By contrast, in the case of a biochip according to an embodiment of the invention, the reaction region that contains catcher molecules and is pervaded by field lines is substantially extended and offers space for a number of target molecules 15 that is greater by a plurality of powers of ten. If an analyte solution 18 is applied to a spot array 3 configured in such a way or to a spot 4, then the target molecules 19 contained in it, which is likewise illustrated only symbolically and with exaggerated size in FIG. 2, find a substantially larger number of possible binding partners in the form of the catcher molecules 15.

The reaction layer 14 is preferably dimensioned, or has a thickness, such that the impedance-spectroscopic detection range is practically fully utilized, which is achieved in any event given a thickness of the reaction layer of approximately 2 to 100 µm and is the case in practice already at 2-10 µm. Consequently, the binding-specific measuring effect of the biochip can be substantially increased given a corresponding concentration of catcher molecules 15 in this region.

The reaction layer 14 is configured such that it provides an aqueous reaction medium. Furthermore, it is configured such that target molecules 19 or else other substances required for a reaction, for example polymerase, can indiffuse into it without its activity being impaired in the process.

As already mentioned above, according to an embodiment of the invention a hydrogel is used as the reaction layer 14. A hydrogel represents an aqueous milieu in a mechanically stable form whilst at the same time ensuring the substance exchange in a predominantly aqueous environment. Through the choice of chemical composition, which relates to the components and the ratio thereof among one another, the properties of the hydrogels such as water content, swelling behavior, mechanical stability etc. can be varied over wide ranges.

A hydrogel that can be produced easily and has a good adhesion both with respect to the electrode arrangement 5 and with respect to the insulating layer 13 is an acrylamide-based radical-crosslinkable hydrogel containing a comonomer enabling a covalent coupling of correspondingly modified catcher molecules via linker groups. The hydrogel includes, in addition to the monomer precursor of polyacrylamide, a crosslinking agent, at least one radical initiator, at least one comonomer with reactive linker groups and, if appropriate, at least one plasticizer.

After layer production and subsequent thermal crosslinking or photocrosslinking, a water-swellable hydrogel is obtained containing reactive linker groups for the immobilization of catcher molecules. Methylene bisacrylamide and/or dimethylacrylates, for example tetraethylene glycol dimethacrylate, are used as crosslinking agents.

The hydrogel mesh size can be set by varying the concentrations of the crosslinking agent. The comonomer used contains maleic anhydride and/or glycidyl (meth)acrylate. Mono-, di- and/or triethylene glycol is suitable as plasticizer. The starting substances mentioned are mixed with a polar, water-miscible solvent, preferably with dimethylformamide.

The processing viscosity can be set by varying the proportion of solvent. The adhesion to the flat carrier surface and also to the electrode arrangement 5 can be reinforced by admixture of customary adhesion promoters, for example silane-based adhesion promoters.

Figure 4:
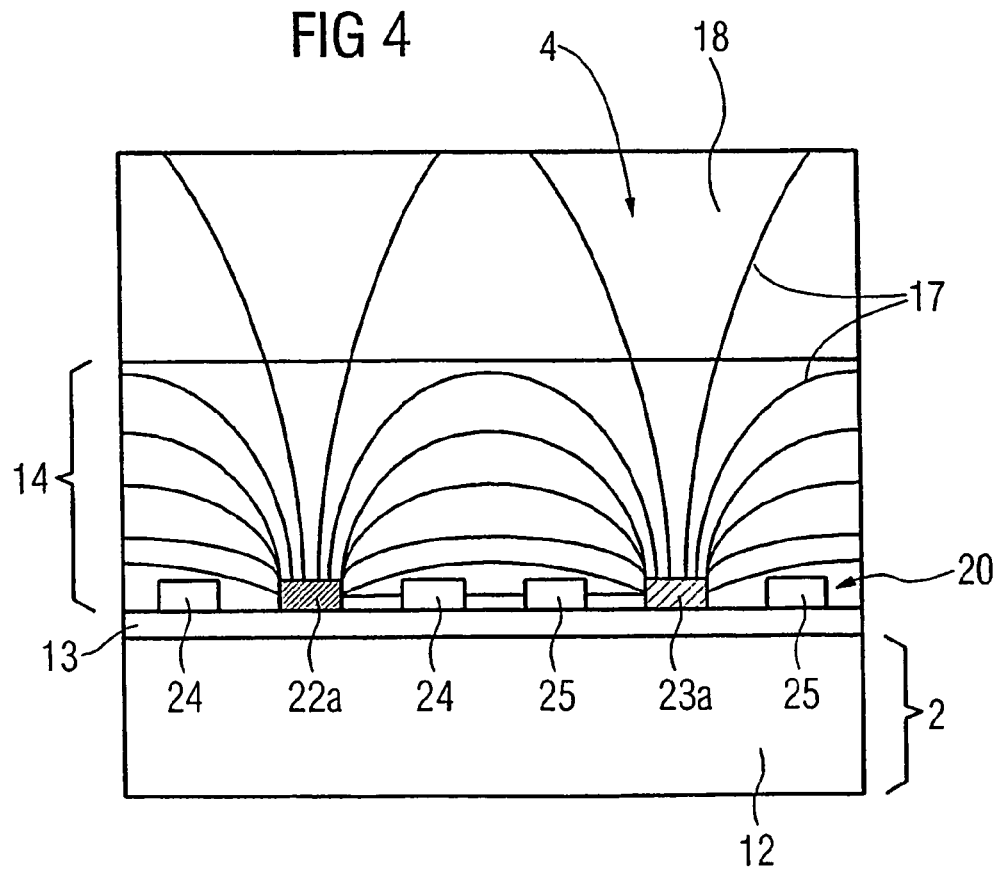
FIG. 4 shows an embodiment of a biochip with a 4-pole electrode arrangement in an illustration corresponding to FIG. 2.
Figure 5:
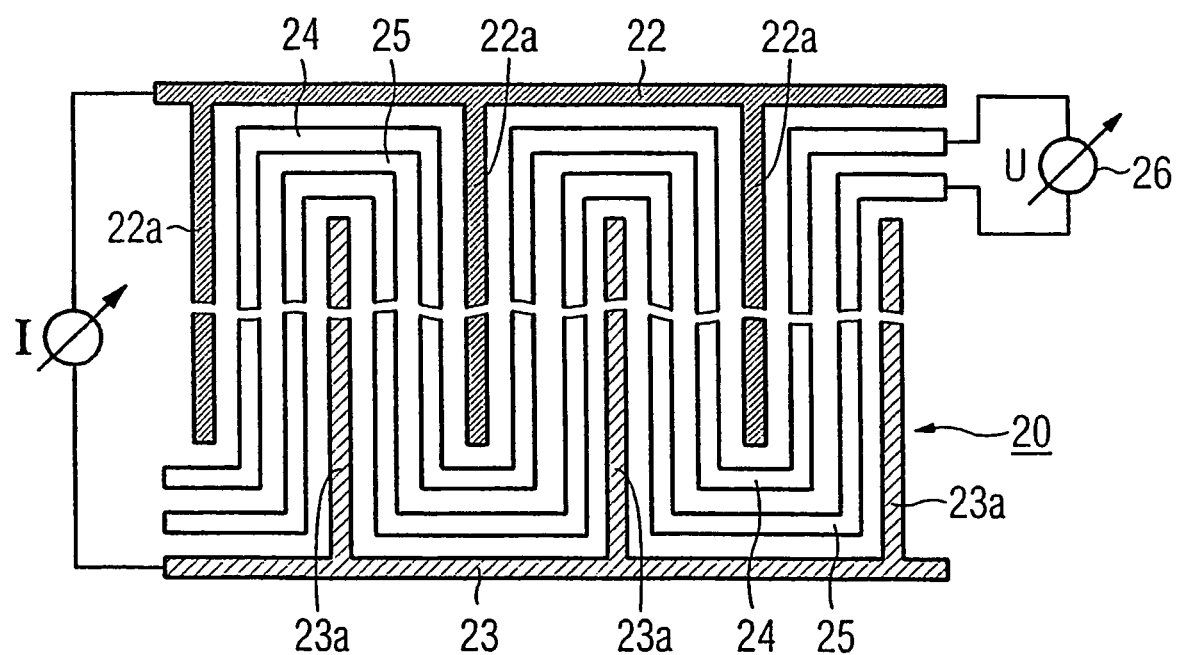
FIG. 5 shows the electrode arrangement of the biochip of FIG. 4 in an illustration corresponding to FIG. 3.

FIGS. 4 and 5 illustrate an exemplary embodiment with a 4-pole electrode arrangement 20. The electrode arrangement 20 is composed of two current electrodes 22, 23 and two voltage or probe electrodes 24, 25. The current electrodes 22, 23 are arranged and configured in accordance with the electrode arrangement 5 of the exemplary embodiment according to FIG. 2.

The probe electrodes 24, 25 are likewise strip-type and extend as a meandering double strand through the interspaces present between the partial electrodes 22a and 23a. A high-frequency AC current is applied to the current electrodes 22, 23. A voltmeter 26 is connected to the probe electrodes 24, 25 and can be used to detect an alteration in the alternating electric field on account of binding events.

The measurement can thus be effected independently of the current electrodes, so that e.g. their polarization that increases the electrode impedance cannot affect the measurement. By contrast, in the case of a 2-pole electrode arrangement, the electrode impedance has to be kept low by means of a correspondingly high measurement frequency that is unfavorable in terms of measurement technology, in order to be able to determine the resistance of the analyte solution or of the reaction layer, which resistance is crucial for the measurement.

A 2-pole electrode arrangement in combination with very high measurement frequencies (>1 MHz) is advantageous for detecting changes in capacitance within the reaction layer that are caused by binding events.

The present invention being thus described, it will be obvious that the same may be varied in many ways. Such variations are not to be regarded as a departure from the spirit and scope of the present invention, and all such modifications are intended to be included within the scope of the present invention.

The invention claimed is:

1. A DNA chip, comprising:
   a flat carrier;
   an array of spots containing catcher molecules, each spot being assigned a microelectrode arrangement for detecting binding events between the catcher molecules and target molecules applied via an analyte solution, wherein the microelectrode arrangement is at least a two-pole system,
   the microelectrode arrangement being at least partially embedded in a hydrophilic reaction layer which is permeable to target molecules and in which immobilized catcher molecules are distributed three-dimensionally, wherein the catcher molecules are configured to cause the binding events,
   the hydrophilic reaction layer having a thickness approximately in the range of 1L to 5 L, L being the sum of electrode width and electrode spacing, the electrode width and the electrode spacing being approximately 1 μm,
   wherein the chip is configured for application of an alternating voltage in a megahertz frequency, and
   wherein the chip is configured to detect a capacitance change caused by the binding events within the hydrophilic reaction layer with a megahertz frequency applied to the electrodes.

2. The DNA chip as claimed in claim 1, wherein the microelectrode arrangement is a two-pole system, and wherein the hydrophilic reaction layer has a thickness of approximately 3 μm.

3. The DNA chip as claimed in claim 1, wherein the microelectrode arrangement is a four-pole system, and wherein the hydrophilic reaction layer has a thickness of approximately 7 μm.

4. The DNA chip as claimed in claim 3, wherein the hydrophilic reaction layer is an acrylamide-based radical-crosslinkable hydrogel including at least one of maleic anhydride and glycidyl (meth)acrylate as coupling groups.

5. The DNA chip as claimed in claim 1, wherein the hydrophilic reaction layer is thermally stable up to approximately 95° C.

6. The DNA chip as claimed in claim 1, wherein the hydrophilic reaction layer contains coupling groups for the covalent binding of catcher molecules.

7. The DNA chip as claimed in claim 1, wherein the microelectrode arrangement is an interdigital electrode arrangement.

8. The DNA chip as claimed in claim 7, wherein the interdigital electrode arrangement is a two-pole microelectrode system.

9. The DNA chip as claimed in claim 7, wherein the interdigital electrode arrangement is a four-pole microelectrode system.

10. The DNA chip as claimed in claim 1, wherein the flat carrier includes a semiconductor layer and an insulating layer connected thereto, the insulating layer carrying the microelectrode arrangement and the hydrophilic reaction layer on its side remote from the semiconductor layer.

11. The DNA chip as claimed in claim 10, wherein the semiconductor layer is a silicon layer.

12. The DNA chip as claimed in claim 1, wherein the hydrophilic reaction layer comprises a hydrogel containing a cross-linking agent.

13. The DNA chip as claimed in claim 12, wherein the cross-linking agent is a dimethylacrylate or methylene bisacrylamide.

14. The DNA chip as claimed in claim 13, wherein the dimethylacrylate is tetraethylene glycol dimethylacrylate.

15. The DNA chip as claimed in claim 12, wherein the hydrophilic reaction layer is thermally cross-linked by the cross-linking agent.

16. The DNA chip as claimed in claim 12, wherein the hydrophilic reaction layer is photo-cross-linked by the cross-linking agent.

* * * * *